United States Patent
Adler

(10) Patent No.: US 10,117,563 B2
(45) Date of Patent: Nov. 6, 2018

(54) POLYP DETECTION FROM AN IMAGE

(71) Applicant: GYRUS ACMI, INC., Southborough, MA (US)

(72) Inventor: Doron Adler, Haifa (IL)

(73) Assignee: GYRUS ACMI, INC., Southborough, MA (US)

( * ) Notice: Subject to any disclaimer, the term of this patent is extended or adjusted under 35 U.S.C. 154(b) by 543 days.

(21) Appl. No.: 14/580,260

(22) Filed: Dec. 23, 2014

(65) Prior Publication Data

US 2015/0190035 A1 Jul. 9, 2015

Related U.S. Application Data

(60) Provisional application No. 61/925,626, filed on Jan. 9, 2014.

(51) Int. Cl.
| | | |
|---|---|---|
| A61B 1/04 | (2006.01) | |
| A61B 1/00 | (2006.01) | |
| C12N 15/10 | (2006.01) | |
| C12Q 1/6806 | (2018.01) | |
| G01N 27/447 | (2006.01) | |
| A61B 1/06 | (2006.01) | |
| G06T 7/00 | (2017.01) | |
| G06T 7/254 | (2017.01) | |
| A61B 1/05 | (2006.01) | |

(52) U.S. Cl.
CPC ........ *A61B 1/00009* (2013.01); *A61B 1/0005* (2013.01); *A61B 1/0676* (2013.01); *C12N 15/101* (2013.01); *C12Q 1/6806* (2013.01); *G01N 27/44791* (2013.01); *G06T 7/0016* (2013.01); *G06T 7/254* (2017.01); *A61B 1/05* (2013.01); *G06T 2207/10068* (2013.01); *G06T 2207/30032* (2013.01)

(58) Field of Classification Search
CPC ..... A61B 1/0005; A61B 1/0676; G06T 7/254; G06T 7/0016; G06T 2207/10068; G06T 2207/30032; C12N 15/101; G01N 27/44791
USPC ........................................................ 600/109
See application file for complete search history.

(56) References Cited

U.S. PATENT DOCUMENTS

| | | | | |
|---|---|---|---|---|
| 4,953,539 A | * | 9/1990 | Nakamura | A61B 1/00177 348/E5.029 |
| 5,633,675 A | * | 5/1997 | Danna | A61B 1/00179 348/65 |
| 5,699,798 A | * | 12/1997 | Hochman | A61B 5/0059 348/164 |

(Continued)

*Primary Examiner* — Timothy J Neal
*Assistant Examiner* — Jae Woo
(74) *Attorney, Agent, or Firm* — D. Kligler I.P. Services Ltd.

(57) ABSTRACT

A method of identifying the presence of a suspect region such as a polyp in a body cavity of a subject includes generating successive images of a body cavity of the subject, and comparing the successive images of the body cavity, wherein a suspect region of the body cavity is likely present when the successive images are different in terms of intensity, surroundings, registration, and/or protrusions. Also provided is an apparatus comprising a processor and an endoscope having a camera and one or more illuminators such that the processor is configured to compare the images acquired from the camera and the one or more illuminators to identify the presence of a suspect region such as a polyp.

8 Claims, 3 Drawing Sheets

(56) References Cited

U.S. PATENT DOCUMENTS

| | | | | |
|---|---|---|---|---|
| 5,827,190 A * | 10/1998 | Palcic | A61B 1/043 600/109 |
| 6,359,644 B1 * | 3/2002 | Salvati | A61B 5/1076 348/65 |
| 6,364,829 B1 * | 4/2002 | Fulghum | A61B 1/00009 600/160 |
| 6,448,545 B1 * | 9/2002 | Chen | A61B 1/042 250/208.1 |
| 6,473,637 B1 * | 10/2002 | Hayashi | A61B 1/043 600/477 |
| 6,488,619 B1 * | 12/2002 | Miyanaga | A61B 1/0008 600/129 |
| 6,510,338 B1 * | 1/2003 | Irion | A61B 1/00186 600/160 |
| 7,289,140 B2 * | 10/2007 | Kobayashi | A61B 1/00009 348/61 |
| 8,423,123 B2 * | 4/2013 | Horn | A61B 1/04 345/419 |
| 8,698,806 B2 * | 4/2014 | Kunert | G06T 15/08 345/419 |
| 8,791,957 B2 * | 7/2014 | Kadomura | A61B 5/055 345/419 |
| 2001/0055462 A1 * | 12/2001 | Seibel | A61B 1/00048 385/147 |
| 2002/0128559 A1 * | 9/2002 | Zigler | A61B 5/4255 600/478 |
| 2002/0139920 A1 * | 10/2002 | Seibel | A61B 1/0008 250/208.1 |
| 2004/0059215 A1 * | 3/2004 | Nishimura | A61B 5/00 600/410 |
| 2004/0162492 A1 * | 8/2004 | Kobayashi | A61B 1/05 600/476 |
| 2004/0245350 A1 * | 12/2004 | Zeng | A61B 1/042 236/43 |
| 2009/0028407 A1 * | 1/2009 | Seibel | A61B 1/0008 382/131 |
| 2009/0074269 A1 * | 3/2009 | Nishimura | A61B 1/04 382/128 |
| 2009/0156900 A1 * | 6/2009 | Robertson | A61B 1/00009 600/160 |
| 2009/0202124 A1 * | 8/2009 | Matsuda | G06T 7/0012 382/128 |
| 2009/0203964 A1 * | 8/2009 | Shimizu | A61B 1/04 600/109 |
| 2009/0244521 A1 * | 10/2009 | Yazdanfar | G01N 21/6456 356/73 |
| 2009/0318800 A1 * | 12/2009 | Gundel | A61B 5/02007 600/425 |
| 2010/0183210 A1 * | 7/2010 | Van Uitert | G06K 9/46 382/131 |
| 2011/0157340 A1 * | 6/2011 | Yamazaki | A61B 1/00009 348/61 |
| 2011/0164064 A1 * | 7/2011 | Tanaka | A61B 5/1075 345/667 |
| 2012/0121144 A1 * | 5/2012 | Tanaka | A61B 1/00009 382/128 |
| 2012/0157775 A1 * | 6/2012 | Yamaguchi | A61B 1/0638 600/180 |
| 2013/0018255 A1 * | 1/2013 | Kitamura | A61B 1/00009 600/424 |
| 2013/0109915 A1 * | 5/2013 | Krupnik | G06T 3/4038 600/109 |
| 2015/0294463 A1 * | 10/2015 | Takahashi | G02B 23/2423 348/71 |
| 2015/0374210 A1 * | 12/2015 | Durr | A61B 1/041 600/111 |
| 2016/0006943 A1 * | 1/2016 | Ratnakar | A61B 1/00009 348/36 |
| 2017/0105613 A1 * | 4/2017 | Tsuruta | A61B 1/0615 |

* cited by examiner

POLYP DETECTION FROM AN IMAGE

CROSS-REFERENCE TO RELATED APPLICATION

This application claims the benefit of U.S. Provisional Application No. 61/925,626, filed Jan. 9, 2014, the entire contents of which are herein incorporated by reference.

FIELD

The embodiments of this invention relate generally to image analysis, and specifically to analyzing successive images of a body cavity to determine the presence of a suspect region such as a polyp in the cavity.

BACKGROUND

Polyp detection in body cavities such as the abdomen or colon is typically performed by a trained professional making a visual inspection of the cavity. A fixed or a flexible endoscope is inserted into the cavity, and the endoscope both illuminates the cavity and acquires images of the illuminated portion of the cavity. The professional views the images, and assesses whether a polyp appears to be present in the illuminated portion.

Detection of a polyp is difficult because of the relatively complicated background that is the surface of the cavity. Consequently, because of the complicated background, even a trained professional may have difficulty in identifying a region as likely to comprise a polyp.

SUMMARY

Embodiments of the present invention provide an indication of the presence of a polyp in a region by comparing successive images of the region. The images are typically generated as a video camera moves in relation to the region. Each successive image of the region is illuminated differently, and the differently illuminated images are compared, typically by subtraction. The subtraction enables highlighting of a suspect section of the region, i.e. an area such as a polyp that protrudes from its surroundings, since in the suspect section the protrusion causes the differences between the two images to be accentuated, compared to the differences of the surroundings.

In a first embodiment of the invention, a camera having two separate illuminators acquires an initial image of the region while the region is illuminated with a first of the illuminators. The camera then acquires a subsequent image of the region while the region is illuminated with a second of the illuminators. The two images are compared as described above to detect the presence of a suspect section in the region.

In a second embodiment of the invention, a camera with a single illuminator moves from a first location to a second location. The camera acquires images of the region in each location, the two images being differently illuminated by virtue of the movement of the camera. As described above the presence of a suspect section in the region is detected by comparing the two images, the protrusion of the suspect section causing the two images to be significantly different.

Either embodiment may be implemented using a video camera that images the body cavity. The second embodiment assumes that the video camera moves between successive images, while in the first embodiment the video camera may move or may be stationary.

BRIEF DESCRIPTION OF THE DRAWINGS

The following figures are presented as an aid to understanding the principles and implementation of embodiments of the present invention and constitute an integral part of this patent application.

DETAILED DESCRIPTION OF SOME EMBODIMENTS

In an embodiment, the invention provides an apparatus for inspecting a body cavity, the apparatus comprising: an endoscope configured to be inserted into the body cavity and comprising a camera and a first illuminator and a second illuminator, wherein the camera is configured to acquire a first image of the body cavity while the cavity is illuminated by the first illuminator and to acquire a second image of the cavity while the cavity is illuminated by the second illuminator; and a processor configured to form a comparison between the second image and the first image, and to identify an area of the body cavity as a suspect region in response to the comparison.

In an embodiment, the invention provides apparatus for inspecting a body cavity, the apparatus comprising: an endoscope configured to be inserted into the body cavity and comprising a camera and an illuminator, wherein the camera is configured to acquire a first image of the body cavity while the cavity is illuminated by the illuminator in a first location and to acquire a second image of the cavity while the cavity is illuminated by the illuminator in a second location; and a processor configured to form a comparison between the second image and the first image, and to identify an area of the body cavity as a suspect region in response to the comparison.

Figure 1:
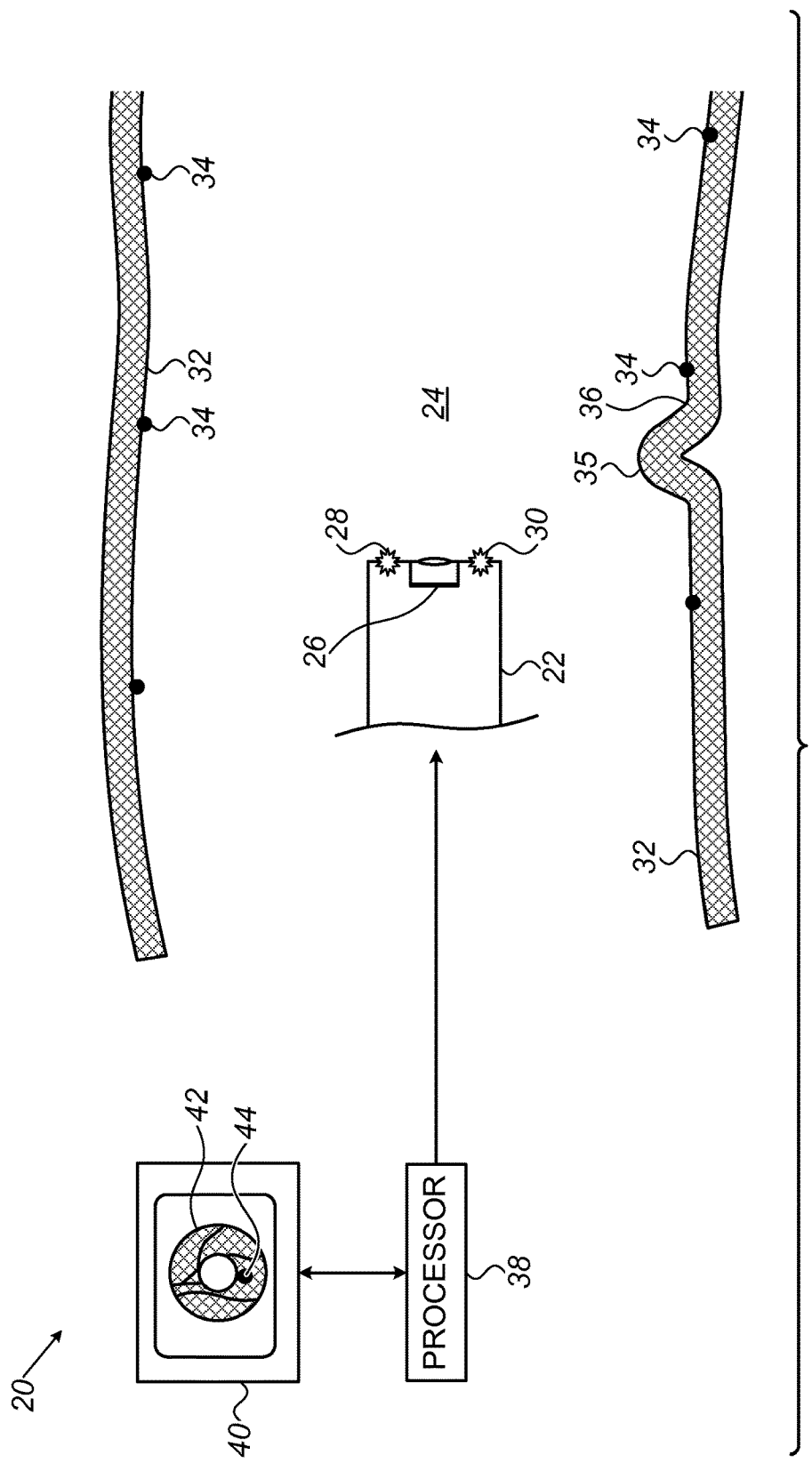
FIG. 1 is a schematic drawing of a suspect region detection system, according to an embodiment of the present invention.

FIG. 1 schematically illustrates a suspect region detection system 20, according to an embodiment of the present invention. While the systems of FIG. 1 and FIG. 2 (described below) may be used to detect many types of suspect region, in the following description, for clarity and simplicity the suspect region is assumed to comprise a polyp.

A distal end of an endoscope 22 comprises a camera 26 and two separate, similar, lights or illuminators 28, 30, and the endoscope is inserted into a body cavity 24 so that its distal end is positioned in proximity to a surface 32 of the cavity. Typically, although not necessarily, the axis of the distal end is approximately parallel to a surface of the body cavity, as is illustrated by way of example in the diagram. However, it will be understood that in practice, since the distal end is being inserted into the cavity, this spatial relationship between the distal end axis and the cavity surface is at best an approximation. Thus, embodiments of the present invention operate regardless of the orientation of the distal end with respect to the body cavity surface, so that the orientation of the distal end may vary from parallel to the surface to perpendicular to the surface. Elements of the endoscope, including the camera and the two separate lights, are controlled by a processor 38, which may be integrated with the endoscope, or which may be separate from the endoscope.

While the description herein refers, for clarity and simplicity, to two illuminators, it will be understood that any plurality of lights may be used in embodiments of the present invention.

Each illuminator 28, 30 is able to illuminate a region of the surface 32 of the body cavity 24, and the camera 26 is configured to acquire images of the region while the region is illuminated. The images may be displayed on a monitor 40, which is under control of the processor 38.

In operation, the two illuminators 28, 30 are toggled, so that the body cavity surface 32 is illuminated in turn by each of the illuminators. (If more than two lights are present, then one or more may be toggled, so that the body cavity surface is differently illuminated as the lights toggle.) As each light illuminates, the camera 26 acquires an image of the illuminated cavity surface 32. If the distal end is stationary with respect to the cavity surface, the two images will be in registration. However, because of the changes in illumination and consequent changes in returning radiation, there will be intensity differences between corresponding regions of the two images. These differences will be accentuated in the region of a polyp 35, which protrudes from the cavity surface, because of the shadowing effect of the protrusion. Thus, by way of example, in the diagram the region 36 of the cavity surface is well illuminated by light 28, but is shadowed by the polyp when illuminated by light 30.

If the distal end of endoscope 22 moves between acquisition of the two images, then there are again differences in intensity between the two images, and these differences are accentuated in the polyp region 36 because of the polyp protrusion. In the case of a moving distal end, in order to make a good comparison of the two images, it may be necessary to register the images. Such registration may be performed by the processor 38, for example by using blood vessels 34 or other visible entities in the cavity surface 32 as registration elements. Additionally or alternatively, while the processor 38 may not "know" that the region of the polyp 36 is in fact a polyp (until after analysis of the two images), it may use features of the polyp region as registration elements.

Regardless of whether registration is needed or not, the processor 38 is able to measure the differences between the two images. As is described in more detail below with respect to the flowchart of FIG. 3, the processor may display an image 42 of the body cavity surface on the monitor 40, and may indicate on the image a suspect region 44 of the image, such as a polyp, where the differences are accentuated.

Figure 2:
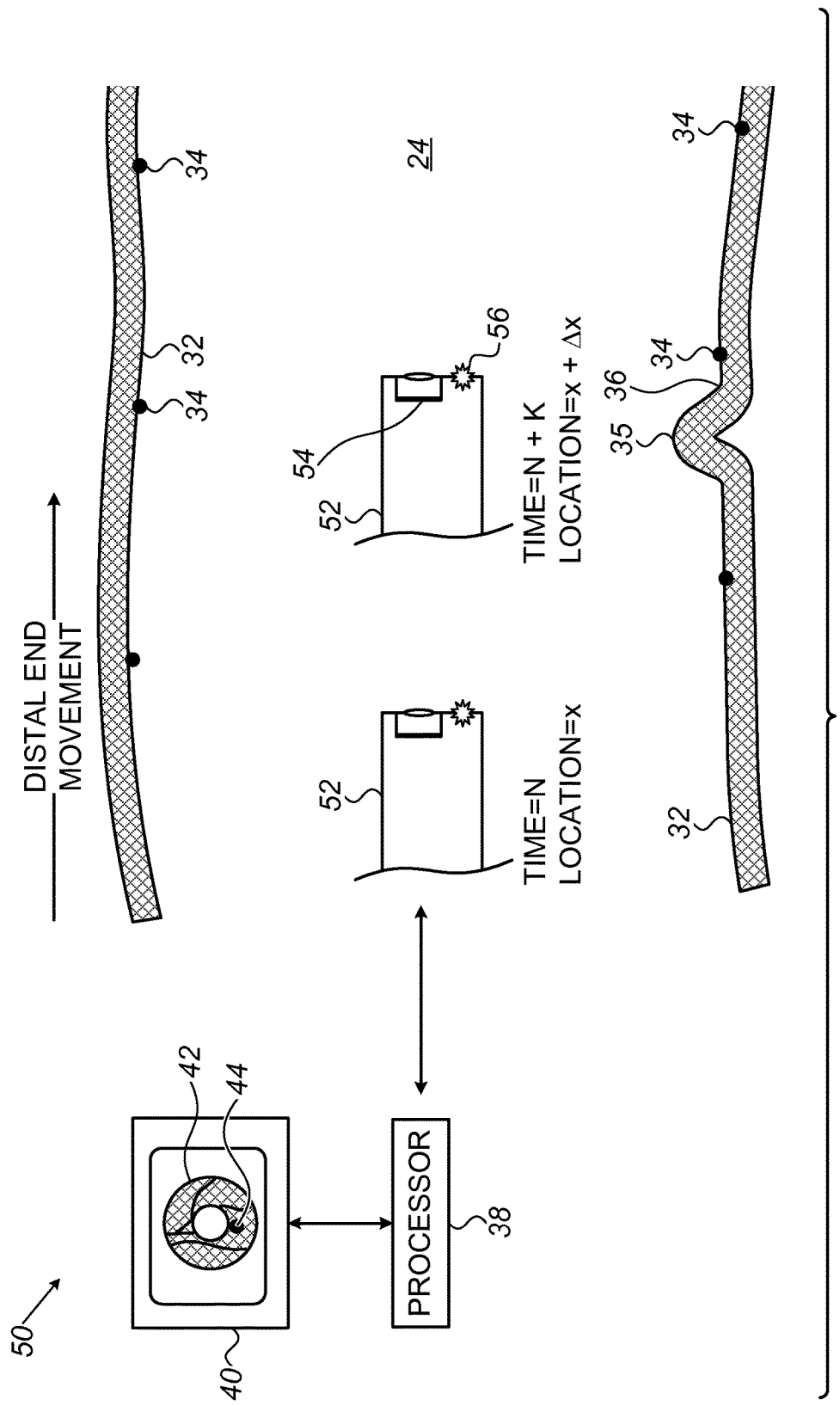
FIG. 2 is a schematic drawing of a suspect region detection system, according to an alternative embodiment of the present invention.

FIG. 2 schematically illustrates an alternative suspect region detection system 50, according to an embodiment of the present invention. Except for the differences described below, the elements of the alternative system illustrated in FIG. 2 are similar to those of the system of FIG. 1, and have similar properties and functionality.

In the alternative system of FIG. 2, the distal end of an endoscope 52 comprises a camera 54 and a single illuminator 56 (in contrast to the two illuminators of the FIG. 1 system). In the alternative system 50, in order to generate two images of the body cavity surface, the distal end moves from a location x at time N to a location x+Δx at time N+K, and the camera 54 acquires images of the body cavity at both locations. As for the system of FIG. 1, in the alternative system of FIG. 2, because of the changes in illumination of the surface 32, there will be intensity differences between the two images. These differences will be accentuated in the region of a polyp 35, which protrudes from the cavity surface, because of the shadowing effect of the protrusion. Thus, in the diagram, the region 36 of the cavity surface is shadowed by the polyp 35 when the distal end of endoscope 52 is in location x, but is well illuminated when the distal end is in location x+Δx.

Figure 3:
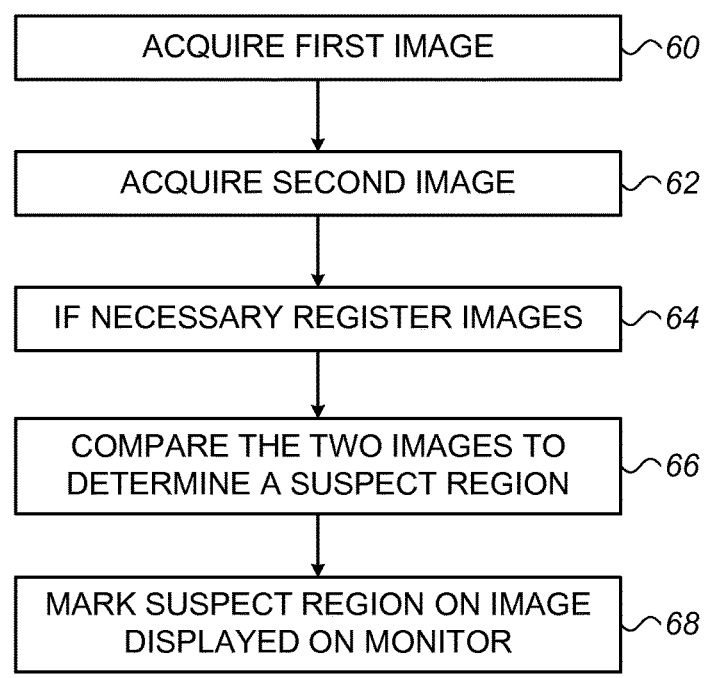
FIG. 3 is a flowchart of steps performed by a processor, using either the system of FIG. 1 or the system of FIG. 2, to identify a suspect region in a body cavity surface, according to an embodiment of the present invention.

FIG. 3 is a flowchart of steps performed by the processor 38, using either the system 20 of FIG. 1 or the system 50 of FIG. 2, to identify a suspect region in a body cavity surface 32, according to an embodiment of the present invention. The steps are described assuming that the endoscope 22 or 52 has been inserted into the body cavity, so that the endoscope distal end is in proximity to the cavity surface 32.

In the first two steps 60, 62 the processor 38 acquires a first image and a second image of the body cavity surface, using the camera 26 or 54 of the system. In the system 20 of FIG. 1, the first image is acquired by illumination with light generated from the first illuminator 28, and the second image is acquired by illumination with light generated from the second illuminator 30. In the system 50 of FIG. 2, the first image is acquired when the distal end of endoscope 52 is in a first position, and the second image is acquired when the distal end has moved from its first position to a second position.

In a registration step 64, the processor 38 registers the two images. (This step may not be necessary in the case of the system 20 of FIG. 1, if the endoscope distal end is stationary.) The registration is typically performed by the processor 38 identifying common elements, such as blood vessels 34 or regions having the same shape in the two images, the latter usually including the region comprising the suspect region. Other methods for registration will be apparent to those having ordinary skill in the art, and all such methods are included in the scope of the present invention. For example, the position and orientation of the distal end in space may be tracked, by methods known in the art, and the registration may then be performed by implementing a spatial transformation of the distal end.

In a comparison step 66 the processor 38 compares the two images in order to identify a suspect region.

In one embodiment the processor 38 generates a three-dimensional (3D) map of the cavity surface 32 from comparison of the two images, and determines that a suspect region is where there is a significant protrusion above the surface. The size of the significant protrusion, in order for its region to be considered suspect, may be determined without undue experimentation.

In an alternative embodiment the processor 38 calculates differences in intensity between corresponding pixels of the two images. The processor then analyzes the differences to find a region 36 of differences that is suspect by being significantly different from its surroundings. Typically the detection of such a region is determined by the processor finding a preset number of contiguous pixels having an average intensity different by a predetermined factor from an image-average difference.

Other methods for determining, from two differently illuminated images, a region that is significantly different from its surroundings, and/or that protrudes from its surroundings, will be apparent to those having ordinary skill in the art, and are included in the scope of the present invention.

In a final step 68 the processor 38 displays one of the two images, typically the second image, on the monitor 40, and marks a suspect region 44 detected in the previous step on the displayed image 42.

Variations on the two embodiments described above will be apparent to a person skilled in the art, and are included within the scope of the present invention. As a first example, in the embodiment illustrated in FIG. 1, rather than attaching two illuminators to the endoscope distal end, at least one of the illuminators may be separated from the distal end, and thus be separated from the distal end camera. As a second example, in the embodiment illustrated in FIG. 2, the illuminator may also be separated from the distal end and thus from the distal end camera. In this case the two images may be acquired by either moving the camera, or by moving the illuminator, or by moving both the camera and the illuminator.

As another example, rather than having illuminators at the distal end, illumination could be transmitted through one or more of the working channels of the endoscope. For example an optical fiber, with or without a lens system at its tip, could be inserted, and could generate different illuminations at the surface 32 as described above. Alternatively or additionally, the angular orientation of the fiber relative to the axis of the distal end could be changed, so that when the fiber is rotated, the illumination will be directed to different angles. The change in illumination caused by the rotation could be used for detection of a suspect region, as described above.

Furthermore, while in the description above the processor 38, to compare images, may calculate intensity differences between corresponding pixels of images, other characteristics of a pixel may be compared. Such characteristics include, but are not limited to, a color of the pixel, or one or more elements of a color, e.g., the red, green, and/or blue level of the pixel, or its hue, saturation, and/or brightness. All such characteristics are included within the scope of the present invention.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art.

What is claimed:

1. A method for inspecting a body cavity, comprising:
    inserting an endoscope into the body cavity, the endoscope comprising a camera and a first illuminator and a second illuminator, similar to the first illuminator, in different, respective locations on the endoscope;
    acquiring with the camera a first image of the body cavity while the cavity is illuminated by the first illuminator and a second image of the cavity while the cavity is illuminated by the second illuminator;
    forming a comparison, by a processor, between the first image and the second image by calculating intensity differences between corresponding pixels of the first image and the second image;
    identifying, by the processor, an area of the body cavity as a suspect region in response to a difference in shadowing between the first and second images that is found in the comparison, by finding in the region a certain number of contiguous pixels for which the intensity differences are greater than an average intensity difference; and
    displaying one of the acquired images on a monitor while marking the suspect region on the one of the acquired images.

2. The method of claim 1, wherein the processor is integrated with the endoscope.

3. The method of claim 1, wherein the processor is separate from the endoscope.

4. The method of claim 1, wherein the processor is configured to form the comparison by calculating color, hue, saturation, and/or brightness differences between the corresponding pixels of the first image and the second image.

5. The method of claim 1, wherein the processor is configured to form the comparison through a registration step for both the first image and the second image.

6. The method of claim 1, wherein the suspect region comprises a polyp.

7. An apparatus for inspecting a body cavity, the apparatus comprising:
    an endoscope configured to be inserted into the body cavity and comprising a camera and a first illuminator and a second illuminator, similar to the first illuminator, in different, respective locations on the endoscope,
    wherein the camera is configured to acquire a first image of the body cavity while the cavity is illuminated by the first illuminator and to acquire a second image of the cavity while the cavity is illuminated by the second illuminator; and
    a processor configured to form a comparison between the second image and the first image by calculating intensity differences between corresponding pixels of the first image and the second image, and
    to identify an area of the body cavity as a suspect region in response to a difference in shadowing between the first and second images that is found in the comparison, by finding in the region a certain number of contiguous pixels for which the intensity differences are greater than an average intensity difference, and
    to display one of the acquired images on a monitor while marking the suspect region on the one of the acquired images.

8. The apparatus of claim 7, wherein the suspect region comprises a polyp.

* * * * *